United States Patent
Li et al.

(10) Patent No.: US 12,029,748 B2
(45) Date of Patent: Jul. 9, 2024

(54) SYNERGISTIC COMPOSITION FOR MAINTENANCE OF HEALTHY BALANCE OF MICROFLORA

(71) Applicant: KIMBERLY-CLARK WORLDWIDE, INC., Neenah, WI (US)

(72) Inventors: Jingru Li, Milton, GA (US); Lindsay A. Peed, Norcross, GA (US); Paige N. Hollmaier, Neenah, WI (US); Rebecca A. Vongsa, Neenah, WI (US); David W. Koenig, Menasha, WI (US); Cheryce F. Joyner, Tallahassee, FL (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/486,220

(22) PCT Filed: Feb. 28, 2017

(86) PCT No.: PCT/US2017/019833
§ 371 (c)(1),
(2) Date: Aug. 15, 2019

(87) PCT Pub. No.: WO2018/160158
PCT Pub. Date: Sep. 7, 2018

(65) Prior Publication Data
US 2020/0009174 A1    Jan. 9, 2020

(51) Int. Cl.
*A61K 31/7068*  (2006.01)
*A61K 31/198*   (2006.01)
*A61K 45/06*    (2006.01)

(52) U.S. Cl.
CPC ........ *A61K 31/7068* (2013.01); *A61K 31/198* (2013.01); *A61K 45/06* (2013.01)

(58) Field of Classification Search
CPC ... A61K 31/7068; A61K 31/198; A61K 45/06
USPC ....................................................... 514/49
See application file for complete search history.

(56) References Cited

U.S. PATENT DOCUMENTS

| | | |
|---|---|---|
| 5,171,575 A | 12/1992 | Shibata et al. |
| 5,176,911 A | 1/1993 | Tosi et al. |
| 5,451,402 A | 9/1995 | Allen |
| 5,466,463 A | 11/1995 | Ford |
| 5,518,733 A | 5/1996 | Lamothe et al. |
| 5,801,116 A | 9/1998 | Cottrell et al. |
| 5,958,104 A | 9/1999 | Nonomura et al. |
| 5,994,326 A | 11/1999 | Matsuda et al. |
| 6,159,465 A | 12/2000 | Adlerberth et al. |
| 6,372,209 B1 | 4/2002 | Chrisope |
| 6,432,440 B1 | 8/2002 | Watts et al. |
| 6,468,526 B2 | 10/2002 | Chrisope |
| 6,521,443 B1 | 2/2003 | Zink et al. |
| 6,632,796 B1 | 10/2003 | Zeng |
| 6,716,435 B1 | 4/2004 | Farmer et al. |
| 6,899,890 B2 | 5/2005 | Kirschner et al. |
| 6,964,949 B2 | 11/2005 | Zeng |
| 6,967,949 B2 | 11/2005 | Davis et al. |
| 7,179,458 B2 | 2/2007 | Chang et al. |
| 7,182,954 B1 | 2/2007 | Cote et al. |
| 7,312,067 B2 | 12/2007 | Samuelsson et al. |
| 7,507,402 B1 | 3/2009 | Farmer et al. |
| 7,619,008 B2 | 11/2009 | Yang et al. |
| 7,713,726 B2 | 5/2010 | Farmer |
| 7,786,176 B2 | 8/2010 | Martin et al. |
| 8,137,706 B2 | 3/2012 | Al-Ghazzewi et al. |
| 8,178,746 B2 | 5/2012 | Hildeberg et al. |
| 8,222,020 B2 | 7/2012 | Forsgren Brusk et al. |
| 8,258,250 B2 | 9/2012 | Fevola et al. |
| 8,277,799 B2 | 10/2012 | Farmer |
| 8,445,226 B2 | 5/2013 | Garner et al. |
| 8,460,917 B2 | 6/2013 | Brøndstad et al. |
| 8,551,518 B2 | 10/2013 | Marsh et al. |
| 8,586,549 B2 | 11/2013 | Zhou et al. |

(Continued)

FOREIGN PATENT DOCUMENTS

| | | |
|---|---|---|
| CA | 2490016 | 12/2004 |
| CN | 1451389 A | 10/2003 |

(Continued)

OTHER PUBLICATIONS

Ojala T. et al. Genome Sequence of Lactobacillus crispatus ST1 // Journal of Bacteriology, 2010, vol. 192, No. 13, pp. 3547-3548.
Adlam, Katie, "Lactobacillus plantarum and its biological implications", MicrobeWiki, Oct. 26, 2014.
Domagk et al, "Pentose Fermentation by Lactobacillus plantarum", J. Biol. Chem. 1958, 233:283-286.
MetaCyc, "MetaCyc Pathway: L-arabinose degradation IV", Fulcher CA, SRI International; Jun. 25, 2013.
Chang, C. E. et al., 'Cultivation of Lactobacillus crispatus KLB46 isolated from human vagina', Biotechnology and Bioprocess Engineering, 2001, vol. 6, pp. 128-132, See the whole document.

(Continued)

*Primary Examiner* — Layla D Berry
(74) *Attorney, Agent, or Firm* — KIMBERLY-CLARK WORLDWIDE, INC.

(57) ABSTRACT

The present invention relates to compositions, particularly compositions useful in maintaining and supporting healthy microflora in the female urogenital tract which could lead to inhibition of vaginal infections, as well as methods of treating and preventing vaginal infections. Compositions useful in supporting healthy microflora, disclosed herein, generally include a first therapeutic agent including α methyl-D glucoside and a second therapeutic agent including a nitrogen containing compound at a therapeutic amount. In some embodiments, the nitrogen containing compound can be, for example, L-Cysteine, Cytidine, D-Asparagine, Pyrimidine, D-Alanine, D-Glucosamine HCL, and N-Acetyl-D-Glucosamine.

13 Claims, No Drawings

(56) References Cited

U.S. PATENT DOCUMENTS

| | | |
|---|---|---|
| 8,609,630 B2 | 12/2013 | Brown |
| 8,632,766 B2 | 1/2014 | Heczko et al. |
| 8,642,029 B2 | 2/2014 | Wang et al. |
| 8,703,179 B2 | 4/2014 | Boga et al. |
| 8,821,854 B2 | 9/2014 | Farmer et al. |
| 8,853,382 B2 | 10/2014 | Hammarstrom et al. |
| 8,871,244 B2 | 10/2014 | Andersch |
| 8,906,668 B2 | 12/2014 | Henn et al. |
| 8,961,945 B2 | 2/2015 | Fevola et al. |
| 2002/0090365 A1 | 7/2002 | Chrisope |
| 2005/0064527 A1 | 3/2005 | Levy et al. |
| 2005/0175630 A1 | 8/2005 | Raz et al. |
| 2005/0175640 A1 | 8/2005 | Yamada et al. |
| 2005/0276836 A1 | 12/2005 | Wilson et al. |
| 2006/0067921 A1 | 3/2006 | Conway |
| 2006/0105963 A1 | 5/2006 | Yang et al. |
| 2006/0154874 A1 | 7/2006 | Hansen |
| 2007/0111965 A1 | 5/2007 | Kipp et al. |
| 2007/0286893 A1 | 12/2007 | Marsh et al. |
| 2008/0107776 A1 | 5/2008 | Prakash et al. |
| 2008/0206188 A1 | 8/2008 | Alverdy et al. |
| 2008/0300558 A1 | 12/2008 | Brusk et al. |
| 2009/0028839 A1 | 1/2009 | Tchikindas et al. |
| 2009/0036849 A1 | 2/2009 | Gustafson et al. |
| 2009/0291069 A1 | 11/2009 | Mastrodonato |
| 2010/0055153 A1 | 3/2010 | Majmudar |
| 2011/0105448 A1 | 5/2011 | Dhuppad et al. |
| 2011/0118686 A1 | 5/2011 | Vega et al. |
| 2011/0124594 A1 | 5/2011 | Bou Antoun |
| 2012/0027838 A1 | 2/2012 | Gordon et al. |
| 2012/0058181 A1 | 3/2012 | Currie et al. |
| 2012/0172831 A1 | 7/2012 | Darcy et al. |
| 2012/0201796 A1 | 8/2012 | Beasley et al. |
| 2012/0258126 A1 | 10/2012 | Schøller et al. |
| 2013/0022586 A1 | 1/2013 | Versalovic et al. |
| 2014/0017340 A1 | 1/2014 | Choi et al. |
| 2014/0037758 A1 | 2/2014 | Choi et al. |
| 2014/0273144 A1 | 9/2014 | Hawkins et al. |
| 2015/0004225 A1 | 1/2015 | Pillay et al. |
| 2015/0018353 A1 | 1/2015 | Kim et al. |
| 2015/0223466 A1 | 8/2015 | Malefyt |
| 2016/0243172 A1 | 8/2016 | Cook et al. |
| 2016/0375045 A1 | 12/2016 | Zeng et al. |
| 2018/0250318 A1 | 9/2018 | Li et al. |
| 2018/0256615 A1 | 9/2018 | Li et al. |
| 2020/0085994 A1 | 3/2020 | Vega et al. |

FOREIGN PATENT DOCUMENTS

| | | |
|---|---|---|
| CN | 1761406 A | 4/2006 |
| CN | 1984990 A | 6/2007 |
| CN | 101411714 A | 4/2009 |
| CN | 1802101 B | 4/2010 |
| CN | 102123736 A | 7/2011 |
| CN | 102370598 A | 3/2012 |
| CN | 102559561 A | 7/2012 |
| CN | 102870987 A | 1/2013 |
| CN | 103189499 A | 7/2013 |
| CN | 103255679 A | 8/2013 |
| CN | 103053900 B | 4/2016 |
| DE | 3510531 A1 | 10/1986 |
| EP | 0257007 B1 | 10/1992 |
| EP | 0773781 B1 | 10/2003 |
| EP | 1633857 B1 | 7/2008 |
| EP | 1946760 A1 | 7/2008 |
| EP | 1481666 B1 | 10/2010 |
| EP | 2314283 A1 | 4/2011 |
| EP | 2353601 A1 | 8/2011 |
| IN | 00404MU2002 A | 2/2004 |
| JP | 63309269 A | 12/1988 |
| JP | 2000189109 A | 7/2000 |
| JP | 2004026725 A | 1/2004 |
| JP | 2006191830 A | 7/2006 |
| JP | 2009517030 A | 4/2009 |
| JP | 4553604 B2 | 9/2010 |
| JP | 2011157348 A | 8/2011 |
| JP | 2013018757 A | 1/2013 |
| KR | 20140046462 A | 4/2014 |
| RU | 2095073 C1 | 11/1997 |
| RU | 2473347 C1 | 1/2013 |
| RU | 2484669 C1 | 6/2013 |
| WO | 9729762 A1 | 8/1997 |
| WO | 9729763 A1 | 8/1997 |
| WO | 9846206 A1 | 10/1998 |
| WO | 9846261 A1 | 10/1998 |
| WO | 2004052121 A1 | 6/2004 |
| WO | 04064850 A1 | 8/2004 |
| WO | 04076615 A2 | 9/2004 |
| WO | 05060937 A1 | 7/2005 |
| WO | 05087270 A1 | 9/2005 |
| WO | 05112567 A2 | 12/2005 |
| WO | 2006000421 A2 | 1/2006 |
| WO | 2006005464 A2 | 1/2006 |
| WO | 06030100 A1 | 3/2006 |
| WO | 2006134409 A2 | 12/2006 |
| WO | 2007117175 A1 | 10/2007 |
| WO | 08100375 A2 | 8/2008 |
| WO | 10056685 A2 | 5/2010 |
| WO | 10061284 A2 | 6/2010 |
| WO | 10062707 A1 | 6/2010 |
| WO | 2010108314 A1 | 9/2010 |
| WO | 11005756 A1 | 1/2011 |
| WO | 11041938 A1 | 4/2011 |
| WO | 2012077038 A1 | 6/2012 |
| WO | 2012101500 A1 | 8/2012 |
| WO | 14012805 A1 | 1/2014 |
| WO | 14026707 A1 | 2/2014 |
| WO | 14027006 A1 | 2/2014 |
| WO | 14106541 A1 | 7/2014 |
| WO | 14113693 A1 | 7/2014 |
| WO | 2015132470 A1 | 9/2015 |
| WO | 2015135470 A1 | 9/2015 |
| WO | 2016149687 A1 | 9/2016 |

OTHER PUBLICATIONS

Van Zanten G.C. et al. The effect of selected synbiotics on microbial composition and short-chain fatty acid production in a model system of the human colon // PLoS One.—2012.

Giannenas, I.A. et al., Journal of Animal and Feed Sciences, "The effects of benzoic acid and essential oil compounds in combination with protease on performance of chickens", 2014, vol. 23, pp. 73-81.

Laniewski, P. et al., Sexually Tranmitted Diseases, "Clinical and Personal Lubricants impact the Growth of Vaginal Lactobacillius Species and Colonization of Vaginal Epithelial Cells: An in Vitro Study", 2021, vol. 48, No. 1, pp. 63-70.

Stanojevic, D.L. et al., Bulgarian Journal of Agricultural Sciene, "Antimicrobial Effects of Sodium Benzoate, Sodium Nitrite and Potassium Sorbate and Their Synergistic Action In Vitro", 2009, vol. 15, No. 4, pp. 307-311.

Hartemink, Ralf, "Prebiotic effects of non-digestible oligo- and polysaccharides", 1999, Agricultural University. Promotor(en): F.M. Rombouts; M.J.R. Nout.—S.I. : S.n.—ISBN 9789058080516-205, https://library.wur.nl/WebQuery/wurpubs/fulltext/196578.

Karlton-Senaye, B. et al., "Synergistic Effect of Polysaccharide Gums and Antimicrobial Agents on Susceptiblity and Protein Expression of Select Pathogenic Microorganisms in Milk", Journal of Food Research, 2018, vol. 7, No. 2, pp. 35-53. (Year: 2018).

Thitaram, Sutawee Narint, "The effect of isomaltooligosaccharide on Bifidobacterium spp. population in young broiler chickens", 2004, Doctoral dissertation, University of Georgia, https://getd.libs.uga.edu/pdfs/thitaram_sutawee_n_200408_ms.pdf.

Skippy, "Strawberry Jam", Mintel Group Limited, Jan. 2014, https://www.gnpd.com/sinatra/recordpage/2292559/from_search/ZJIIQKeLV3/?page=1.

Greenberg, E.P et al., "Chemotaxis in Spirochaeta aurantia", Journal of Bacteriology, Apr. 1977, pp. 485-494, http://europepmc.org/backend/ptpmcrender.fcgi?accid=PMC235227&blobtype=pdf.

(56) References Cited

OTHER PUBLICATIONS

Pezente, L. G., "Caracteristicas glicidicas e microbiologicas de meis de Apis mellifera produzidos em Roraima", Dissertacao de Mestrado em Ciencias Ambientais, Universidade Federal De Roraima, 117 p. 2011, http://repositorio.ufrr.br:8080/jspui/bitstream/prefix/308/1/Caracter%c3%adsticas%20glic%c3%addicas%20e%20microbiol%c3%b3gicas%20de%20m%c3%a9is%20de%20Apis%20mellifera%20produzidos%20em%20Roraima.pdf.

SYNERGISTIC COMPOSITION FOR MAINTENANCE OF HEALTHY BALANCE OF MICROFLORA

BACKGROUND OF THE DISCLOSURE

Humans are colonized by microbes in the gastrointestinal tract, on the skin, and in other epithelial and tissue niches such as the oral cavity, eye surface and vagina. In healthy persons a single local or tissue type may be inhabited by hundreds of different species of bacteria. Interactions between various bacteria species in these populations and between bacteria and the human host shape the community structure with availability of and competition for resources affecting the distribution of various species of bacteria. Such resources may be food, location and the availability of space to grow or a physical structure to which the bacteria may attach.

A healthy microbial flora provides the host with multiple benefits, including colonization resistance to a broad spectrum of pathogens, essential nutrient biosynthesis and absorption, and immune stimulation. For example, a normal vagina generally contains more than about $10^4$ lactobacilli per milliliter of vaginal fluid. Under normal conditions, the vagina flora provides a mildly acidic environment that helps guard against the invasion of pathogenic microbes. Unfortunately, this vaginal balance may be easily upset by a variety of external factors that ultimately lead to vaginal infection. Vaginal infection is a clinical syndrome and exists in three primary forms, i.e., bacterial vaginosis, candidal vaginitis ("yeast"), and trichomonas vaginitis ("trich").

Current treatment regimens for bacterial infection of the vagina involve the use of various broad spectrum antibiotics, such as metronidazole. However, antibiotics are often undesirable because they may kill a broad range of the normal bacterial flora in the vagina, including the beneficial lactobacilli. This may cause secondary complications, because the lactobacilli keep various opportunistic pathogens in the vagina in check. The treatment may then necessitate a further treatment regimen, such as the ingestion of cultured dairy products to replace the lactobacilli in the body, as well as treatment by antifungal agents. Moreover, a rise in the level of anaerobes due to a lack of lactobacilli could further complicate the infection. Additionally, antibiotics, when used frequently within the vagina, may cause systemic toxicity through absorption from the vagina.

As such, a need currently exists for improved compositions for supporting and maintaining a healthy balance of microflora in the urogenital area and more particularly improved vaginal treatment compositions.

SUMMARY OF THE DISCLOSURE

It has now been surprisingly discovered that the growth of certain strains of *Lactobacilli* may be synergistically increased by administering a composition comprising a first therapeutic agent comprising α methyl-D glucoside and a second therapeutic agent comprising certain nitrogen containing compounds. Increasing the growth of beneficial lactobacilli may effectively inhibit the growth of pathogens associated with urogenital infections and help maintain a healthy microflora balance in the urogenital area. As such, these compositions are well suited for topical administration to the urogenital area of a female for supporting and maintaining a healthy balance of microflora in the urogenital area. For example, providing a composition comprising a first therapeutic agent comprising α methyl-D glucoside and a second therapeutic agent comprising certain nitrogen containing compounds synergistically promotes the growth of Lactobacillus spp. without promoting growth of pathogenic bacteria such as *Escherichia coli* (*E. coli*).

Accordingly, in one embodiment a composition can include a first therapeutic agent including α methyl-D glucoside. The composition can include a second therapeutic agent comprising a nitrogen containing compound. The nitrogen containing compound can be selected from the group consisting of L-Cysteine, Cytidine, D-Asparagine, Pyrimidine, D-Alanine, D-glucosamine HCL, and N-Acetyl-D-Glucosamine.

In another embodiment, a composition can include a first therapeutic agent comprising α methyl-D glucoside. The composition can also include a second therapeutic agent comprising a nitrogen containing compound. The nitrogen containing compound can be selected from the group consisting of: Alloxan, Ammonium Citrate, Glycine, L-Cysteine, L-Glutamic Acid, L-Glutamine, L-Homoserine, L-Leucine, L-Lysine, L-Methionine, L-Tyrosine, Cytidine, D-Asparagine, Adenosine, H-Ala Thr-OH, D-glucoronamide, Ala-asp, Ala-His, Gly-Met, N-Acetyl-D-Galactosamine, Pyrimidine, L-Serine, Inosine, D-Alanine, N-Acetyl-D-Mannosamine, Gly-Asn, Ala-Glu, D-Galactosamine HCL, D-Glucosamine HCL, DL-a-amino-n-butyric acid, D-mannosamine HCl, Gly-Gln, Gly-Glu, DL Lactamide, Met-Ala, Methyl(2-phenylethyl)amine Hydrochloride, Glycyl-Alanine, DL-gamma-amino-n-butyric acid, and N-Acetyl-D-Glucosamine. A weight ratio between the first therapeutic agent and the second therapeutic agent can be at least about 2:1.

In yet another embodiment, a composition can include a first therapeutic agent comprising a methyl-D glucoside. The composition can further include a second therapeutic agent comprising a nitrogen containing compound. The nitrogen containing compound can be selected from the group consisting of Glycine, L-Cysteine, L-Ornthine, Cytidine, D-Asparagine, Pyrimidine, D-Alanine, D-Glucosamine HCL, DL-a-amino-n-butyric acid, Methyl(2-phenyethyl)amine Hydrochloride, and N-Acetyl-D-Glucosamine. A weight ratio between the first therapeutic agent and the second therapeutic agent is less than about 2:1.

In still another embodiment, a method for maintaining a healthy microflora balance in the urogenital area of a patient in need thereof is disclosed. The method can include topically administering to the urogenital area of the patient a composition including a first therapeutic agent including α methyl-D glucoside and a second therapeutic agent. The second therapeutic agent can include a nitrogen containing compound. The nitrogen containing compound can be selected from the group consisting of Alloxan, Ammonium Citrate, Glycine, L-Cysteine, L-Glutamic Acid, L-Glutamine, L-Homoserine, L-Leucine, L-Lysine, L-Methionine, L-Ornthine, L-Tyrosine, Cytidine, D-Asparagine, Adenosine, H-Ala-Thr-OH, D-glucoronamide, Ala-Asp, Ala-His, Gly-Met, N-Acetyl-D-Galactosamine, Pyrimidine, L-Serine, Inosine, D-Alanine, N-Acetyl-D-Mannosamine, Gly-Asn, Ala-Glu, D-Galactosamine HCL, D-glucosamine HCL, DL-a-amino-n-butyric acid, D-mannosamine HCL, Gly-Gln, Gly-Glu, DL Lactamide, Met-Ala, Methyl(2-phenylehtyl)amine Hydrochloride, Glycyl-Alanine, DL-gamma-amino-n-butyric acid, and N-Acetyl-D-Glucosamine. The administration of the composition can increase lactobacillus growth or activity in vivo relative to *E. coli*.

Definitions

As used herein, the term "inhibit" generally means to reduce by a measurable amount or to prevent entirely.

As used herein the term "urogenital" refers to the vulva, vagina, urinary tract, bladder, and surrounding areas.

As used herein the terms "effective amount" and "therapeutic amount" is an amount sufficient to maintain and support a healthy balance of microflora. In fact, although not required, it may be desired to use a concentration that does not significantly affect or inhibit the growth characteristics of the normal vaginal flora or otherwise significantly irritate the vaginal tissue when used at inhibitory, noncytotoxic, or clinical concentrations. For example, the therapeutic agent(s) are desirably employed at a concentration of about 0.01 to about 20.0 wt/vol %, in some embodiments from about 0.1 wt/vol % to about 10.0 wt/vol %, in some embodiments from about 0.2 to about 5.0 wt/vol %, and in some embodiments from about 0.5 to about 4.5 wt/vol %. It should be understood that the dosage may vary with the age, condition, and type of infection suffered by the patient, and may be readily determined by one of skill in the art.

As used herein the term "therapeutic effect" refers to the ability of the compositions and formulations of the present invention to stimulate the growth of *Lactobacillus* relative *E. coli* measured according to the Therapeutic Effect Protocol described below. Generally, therapeutic effect is expressed as a ratio of *Lactobacillus* to *E. coli* and is desirably greater than about 2, more preferably greater than about 20 and more desirably greater than about 100.

As used herein, the designation "wt/vol %" or "wt/vol" refers to the value obtained by dividing the weight of a substance (in grams) by the volume of the solution (in milliliters), and then multiplying by 100.

As used herein the term "saccharide" generally refers to a polysaccharide, an oligosaccharide, or a monosaccharide. Frequently, references to a saccharide refers to a monosaccharide, such as α methyl-D glucoside, a disaccharide, such as lactulose, trehalose, rhamnose maltose, maltotriose, lactose and lactitol, a cyclodextrin, pectin, or a non-digestible polysaccharide.

DETAILED DESCRIPTION OF THE DISLOSURE

The present invention is related to compositions useful in maintaining and supporting healthy microflora. The compositions are particularly well suited for administration to the urogenital tract to support and maintain a healthy microflora. Additionally, the compositions and formulations of the present invention may be useful in supporting and maintaining healthy microflora balance on the following applications, but are not limited to such applications, on the skin, in the bladder, or the gastro-intestinal tract. For example, maintenance and support of a healthy microflora may be achieved by topically administering a composition to the urogenital tract or other area of the body. In other embodiments the compositions of the present invention may be formulated for oral administration and orally administered to a patient to support and maintain healthy microflora in the gastro-intestinal tract.

Compositions useful in supporting and maintaining healthy microflora generally comprise a therapeutic amount of a first therapeutic agent comprising α methyl-D glucoside and a therapeutic amount of a second therapeutic agent comprising a nitrogen containing compound. It was discovered during extensive testing, as described further herein, that various carbon sources tested independently and various nitrogen containing compounds tested independently were not able to provide a therapeutic effect, however, combinations of a first therapeutic agent comprising α methyl-D glucoside in combination with certain second therapeutic agents comprising a nitrogen containing compound worked synergistically to provide to provide a therapeutic effect.

Urogenital treatment compositions of the present invention generally stimulate the growth of healthy, native bacteria such as Lactobacillus spp. and may be administered in several forms to a user. For example, the urogenital compositions may be prepared as formulations for administration to a user or may be applied to a substrate, such as a wiping substrate, for administration to a user. Preferably, the compositions useful in the present disclosure are soluble to facilitate their formulation for administration to a user.

Surprisingly, compositions comprising a first therapeutic agent comprising α methyl-D glucoside and a second therapeutic agent comprising a nitrogen containing compound synergistically promote the growth of healthy bacteria such as Lactobacillus spp. and more particularly *Lactobacillus crispatus* without promoting growth of pathogenic bacteria, such as *E. coli*. Accordingly, compositions of the present disclosure may be administered to a user to synergistically and selectively stimulate growth of lactobacilli without stimulating the growth of competing pathogenic bacteria. Thus, in-use, administration of a formulation comprising α methyl-D glucoside and certain nitrogen containing compounds may enhance the growth and colonization of healthy bacteria such as Lactobacillus spp. in the user, which thereby helps reduce the incidence of disease.

The first therapeutic agent can be α methyl-D glucoside. As noted above, various other saccharides that were tested were not able to provide a therapeutic effect, either by themselves or when tested with a second therapeutic agent comprising a nitrogen containing compound. This testing included experimentation with D-arabinose (monosaccharide) and stachyose (polysaccharide).

The second therapeutic agent comprises a nitrogen containing compound. Through extensive testing, however, it was surprisingly discovered that not all nitrogen containing compounds were effective at providing a synergistic, therapeutic effect with the first therapeutic agent comprising α methyl-D glucoside.

Table 1 shows the list of nitrogen containing compounds that were tested along with α methyl-D glucoside for whether they provided a therapeutic effect, or in other words, helped maintain or support a healthy balance of microflora as defined above. The data in Table 1 was tested according to the Therapeutic Effect Protocol as described further herein. The nitrogen compounds were tested for their therapeutic efficacy at three different concentrations when combined with α methyl-D glucoside (1% wt/vol %). The concentrations of the nitrogen containing compounds that were tested were 1% wt/vol %, 0.5% wt/vol %, and 0.1% wt/vol %. Thus, the testing in Table 1 provides ratios of the monosaccharide of α methyl-D glucoside to the nitrogen containing compounds of 1:1 (1% wt/vol. % to 1% wt/vol. %), 2:1 (1% wt/vol. % to 0.5% wt/vol. %), and 10:1 (1% wt/vol % to 0.1% wt/vol %).

Each composition in Table 1 went through initial screening measures of solubility and initial pH ("I pH"). Some compositions including the nitrogen containing compounds at certain wt/vol % ratios were insoluble when combined with the α methyl-D glucoside and other components as noted in the Therapeutic Effect Protocol described herein, and thus, the Therapeutic Efficacy Result is marked as "Insol." for that concentration of the nitrogen containing compound in Table 1. When a specific concentration of a nitrogen containing compound was insoluble, the initial and final pH ("F pH") of the combined composition was not measured and accordingly are each marked as "NM." Additionally, initial pH of the composition was checked as a screening measure. The initial pH was marked as either Low ("L"), High ("H"), or Pass ("P"). A Low initial pH corresponds to an initial pH being less than 5.5, a High initial pH corresponds to an initial pH being greater than 6.5, and a Pass initial pH corresponds to the pH being at or between 5.5-6.5. In compositions including a specific concentration of a nitrogen containing compound combined with the α methyl-D glucoside that provided either a "L" pH or a "H" pH, the therapeutic efficacy result was not measured (marked as "NM") because it is believed that the pH of such a combination could lead to the therapeutic efficacy of the composition, as opposed to the metabolic effects of the carbon and nitrogen sources on the *Lactobacillus* and *E. coli*. As part of the Therapeutic Effect Protocol, a final pH was also measured after the compositions that were tested against the *Lactobacillus* and *E. coli*.

TABLE 1

Therapeutic Efficacy Results for various concentrations of Nitrogen containing compounds with the first therapeutic agent of 1.0 wt/vol % α methyl-D glucoside.

| Nitrogen Compounds | CAS Numbers | Therapeutic Efficacy Results (*Lactobacillus*/*E. coli*) Concentration and pH | | | | | | | | |
|---|---|---|---|---|---|---|---|---|---|---|
| | | 1.00% | I pH | F pH | 0.50% | I pH | F pH | 0.10% | I pH | F pH |
| Allantoin | 97-59-6 | Insol. | NM | NM | 1.37 | P | 4 | 0.9 | P | 4.5 |
| Alloxan | 50-71-5 | NM | L | NM | 1.45E+04 | P | 4 | 4.83 | P | 4.5 |
| Ammonium Chloride Hexahydrate | 7784-13-6 | NM | L | NM | NM | L | NM | NM | L | NM |
| Ammonium Citrate | 3012-65-5 | 3.15E−08 | P | 5 | 4.93E−04 | P | 5.5 | >260 | P | 4 |
| Ammonium Sodium Phosphate | 7783-13-3 | NM | H | NM | NM | H | NM | 0.25 | P | 4.5 |
| D-Arginine | 157-06-2 | Insol. | NM | NM | Insol. | NM | NM | 0.35 | P | 4.5 |
| D-Glutamic Acid | 6893-26-1 | Insol. | NM | NM | NM | L | NM | 1.71 | P | 4.5 |
| D-Serine | 312-84-5 | 0.03 | NM | NM | <1.00 | NM | NM | 0.06 | NM | NM |
| Glycine | 56-40-6 | 950 | P | 5 | 20.5 | P | 5 | 0.56 | NM | NM |
| Hydroxylamine | 7803-49-8 | NM | H | NM | NM | H | NM | 0.20 | H | NM |
| L-Alanine | 56-41-7 | 1.3 | P | 4.5 | 1.52 | P | 4.5 | 1.5 | P | 4.5 |
| L-Arginine | 74-79-3 | Insol. | NM | NM | Insol. | NM | NM | 0.58 | P | 5 |
| L-Asparagine | 70-47-3 | Insol. | NM | NM | 1.72 | P | 4 | 1.12 | P | 4 |
| L-Aspartic Acid | 56-84-8 | Insol. | NM | NM | NM | L | NM | 1.36 | P | 4.5 |
| L-Cysteine | 52-90-4 | 10.44 | P | 4.5 | 28.38 | P | 4 | >299 | P | 4 |
| L-Glutamic Acid | 56-86-0 | NM | L | NM | NM | L | NM | 2.81 | P | 4.5 |
| L-Glutamine | 56-85-9 | 0.53 | P | 4.5 | 1.28 | P | 4.5 | >161 | P | 4 |
| L-Histidine | 71-00-1 | Insol. | NM | NM | Insol. | NM | NM | 1.11 | P | 4.5 |
| L-Homoserine | 672-15-1 | 0.33 | P | 5 | 0.66 | P | 5 | >750 | P | 4 |
| L-Isoleucine | 73-32-5 | Insol. | NM | NM | Insol. | NM | NM | 1.51 | P | 4.5 |
| L-Leucine | 61-90-5 | Insol. | NM | NM | 0.24 | P | 4.5 | 2.9 | P | 4.5 |
| L-Lysine | 657-27-2 | 0.42 | P | 6 | 1.93 | P | 4.5 | >141 | P | 4.5 |
| L-Methionine | 63-68-3 | 0.75 | P | 4.5 | 0.78 | P | 4 | >1.71E+05 | P | 4.5 |
| L-Ornthine | 3184-13-2 | 3.97 | P | 4.5 | 1.24 | P | 4.5 | 1.31 | P | 4 |
| L-Phenylalanine | 63-91-2 | Insol. | NM | NM | Insol. | NM | NM | 0.09 | P | 5 |
| L-Proline | 147-85-3 | 1.25 | P | 4.5 | 0.55 | P | 4.5 | 1.88 | P | 4 |
| L-Threonine | 72-19-5 | 0.36 | P | 5 | 1.13 | P | 4.4 | 0.74 | P | 4.5 |
| L-Tryptophan | 73-22-3 | Insol. | NM | NM | 0.06 | P | 5 | 0.66 | P | 4.5 |
| L-Tyrosine | 60-18-4 | Insol. | NM | NM | Insol. | NM | NM | 2.72 | P | 4.5 |
| L-Valine | 72-18-4 | 1.01 | P | 4.5 | 0.38 | P | 5 | 1.34 | P | 4.5 |
| Uracil | 66-22-8 | Insol. | NM | NM | Insol. | NM | NM | 0.43 | P | 4.5 |
| Cytidine | 65-46-3 | 3.09 | P | 5.5 | 3.85E+03 | P | 4 | >103 | P | 4 |
| D-Asparagine | 2058-58-4 | 72 | P | 4.5 | 6.00E+06 | P | 4 | >3410 | P | 4 |
| Adenosine | 58-61-7 | Insol. | NM | NM | 0.97 | P | 4.5 | <100 | P | 4 |
| H-Ala-Thr-OH | 24032-50-6 | 1.64 | P | 4.5 | >103 | P | 4 | 212 | P | 3.5 |
| D-glucoronamide | 3789-97-7 | 1.6 | P | 4 | 6.84E+03 | P | 4 | >122 | P | 4 |
| Ala-Asp | 20727-65-5 | NM | L | NM | NM | L | NM | >100 | P | 4 |
| Ala-His | 3253-17-6 | NM | H | NM | 6.59E+02 | P | 4 | >133 | P | 4.5 |
| Gly-Met | 554-94-9 | 0.81 | P | 4.5 | >2343.75 | P | 4 | 238 | P | 3.5 |
| N-Acetyl-D-Galactosamine | 1811-31-0 | 0.65 | P | 5.5 | >100 | P | 4.5 | 130 | P | 3.5 |
| Histamine | 51-45-6 | NM | H | NM | NM | H | NM | NM | H | NM |
| Pyrimidine | 289-95-2 | 4.05 | P | 4.5 | >4760 | P | 4 | 245 | P | 3.5 |
| Adenine | 73-24-5 | Insol. | NM | NM | Insol. | NM | NM | Insol. | NM | NM |
| L-Serine | 56-45-1 | 0.45 | P | 4.5 | >299 | P | 4 | 393 | P | 3.5 |
| Inosine | 58-63-9 | 0.45 | P | 4.5 | 226 | P | 4 | 2.75E+04 | P | 3.5 |
| D-Alanine | 338-69-2 | 60 | P | 4.5 | >1.30E+04 | P | 4.5 | 1.10E+06 | P | 3.5 |
| D-Apartic Acid | 1783-96-6 | Insol. | NM | NM | Insol. | NM | NM | NM | L | NM |
| N-Acetyl-D-Mannosamine | 4773-29-9 | 0.02 | P | 5 | 100 | P | 5 | 0.854 | P | 5 |
| Gly-Asn | 1999-33-3 | 1.3 | P | 4.5 | >1.58E+04 | P | 4.5 | 108 | P | 4 |
| Ala-Glu | 13187-90-1 | NM | L | NM | NM | L | NM | 10.67 | P | 3.5 |
| D-Galactosamine HCL | 1772-03-8 | 1.29 | P | 4.5 | >1220 | P | 4 | 6.72 | P | 3.5 |

TABLE 1-continued

Therapeutic Efficacy Results for various concentrations of Nitrogen containing
compounds with the first therapeutic agent of 1.0 wt/vol % α methyl-D glucoside.

| Nitrogen Compounds | CAS Numbers | Therapeutic Efficacy Results (*Lactobacillus/E. coli*) Concentration and pH | | | | | | | | |
|---|---|---|---|---|---|---|---|---|---|---|
| | | 1.00% | I pH | F pH | 0.50% | I pH | F pH | 0.10% | I pH | F pH |
| D-Glucosamine HCL | 66-84-2 | 454 | P | 3.5 | 6.00E+06 | P | 4 | 77.8 | P | 3 |
| DL-a-amino-n-butyric acid | 2835-81-6 | 4.44 | P | 5.5 | 100 | P | 4.5 | 0.34 | P | 4.5 |
| D-mannosamine HCl | 5505-63-5 | 0.96 | P | 5.5 | 84 | P | 5 | 0.202 | P | 5 |
| Gly-Gln | 172669-64-6 | 0.38 | P | 4.5 | >189 | P | 4.5 | 8.57 | P | 4 |
| Gly-Glu | 7412-78-4 | NM | L | NM | NM | L | NM | 6.83 | P | 3.5 |
| DL Lactamide | 65144-02-7 | 0.8 | P | 4 | >1330 | P | 4 | 7.52 | P | 4 |
| n-phthaloyl-l-glutamic acid | 340-90-9 | NM | L | NM | NM | L | NM | NM | L | NM |
| Met-Ala | 3061-96-9 | NM | L | NM | NM | L | NM | 7.33 | P | 4 |
| Methyl(2-phenylethyl)amine Hydrochloride | 4014-43-2 | 3 | P | 5.5 | <1.00 | P | 5 | 10 | P | 4 |
| Glycyl-Alanine | 3695-73-6 | 1.49 | P | 4 | 220 | P | 3.5 | 0.803 | P | 4 |
| DL-gamma-amino-n-butyric acid | 56-12-2 | 1.86 | P | 4.5 | 246.6 | P | 3.5 | 0.836 | P | 4 |
| Ethylenediamine | 107-15-3 | NM | H | NM | NM | H | NM | NM | H | NM |
| N-Amylamine | 110-58-7 | NM | H | NM | NM | H | NM | NM | H | NM |
| N-Acetyl-D-Glucosamine | 7512-17-6 | 7.00E+06 | P | 3.5 | 211 | P | 3 | 8.33 | P | 3.5 |

As shown in Table 1, not all nitrogen containing compounds in combination with the α methyl-D glucoside provided a therapeutic effect (where a ratio of *Lactobacillus* to *E. coli* is greater than 2). Some nitrogen containing compounds in combination with α methyl-D glucoside provided a therapeutic effect where a ratio of *Lactobacillus* to *E. coli* is greater than 2 at each of its concentrations tested. Specifically, the nitrogen containing compounds of L-Cysteine, Cytidine, D-Asparagine, Pyrimidine, D-Alanine, D-Glucosamine HCL, and N-Acetyl-D-Glucosamine in combination with α methyl-D glucoside provided a therapeutic effect at the concentrations of the nitrogen containing compounds of 1 wt/vol %, 0.5 wt/vol %, and 0.1 wt/vol. %. Such nitrogen containing compounds are thus more versatile in the aspect that the specific ratio with α methyl-D glucoside does not affect their ability to provide a therapeutic effect. In some embodiments, it would be preferable to have a composition including a first therapeutic agent including α methyl-D glucoside and a second therapeutic agent of a nitrogen containing compound listed immediately above wherein the ratio between the first therapeutic agent and the second therapeutic agent is from about 0.5:1 to about 20:1, or more preferably from about 1:1 to about 10:1.

Other nitrogen containing compounds in combination with α methyl-D glucoside provided a therapeutic effect only at specific ratios between α methyl-D glucoside and the nitrogen containing compound. For example, the following nitrogen containing compounds in combination with α methyl-D glucoside provided a therapeutic effect when the ratio between the α methyl-D glucoside and the nitrogen containing compound is at least about 2:1, but not at a ratio of 1:1: Alloxan, Ammonium Citrate, Glycine, L-Glutamic Acid, L-Glutamine, L-Homoserine, L-Leucine, L-Lysine, L-Methionine, L-Tyrosine, Adenosine, H-Ala Thr-OH, D-glucoronamide, Ala-asp, Ala-His, Gly-Met, N-Acetyl-D-Galactosamine, L-Serine, Inosine, N-Acetyl-D-Mannosamine, Gly-Asn, Ala-Glu, D-Galactosamine HCL, DL-a-amino-n-butyric acid, D-mannosamine HCl, Gly-Gln, Gly-Glu, DL Lactamide, Met-Ala, Methyl(2-phenylethyl)amine Hydrochloride, Glycyl-Alanine, and DL-gamma-amino-n-butyric acid. The nitrogen containing compounds of Alloxan, H-Ala Thr-OH, D-glucoronamide, Ala-His, Gly-Met, N-Acetyl-D-Galactosamine, L-Serine, Inosine, Gly-Asn, D-Galactosamine HCL, Gly-Gln, and DL Lactamide in combination with α methyl-D glucoside provided a therapeutic effect when the ratio between the α methyl-D glucoside and the nitrogen containing compound was 2:1 and 10:1, but not at a ratio of 1:1.

Furthermore, table 1 also shows that very few of the nitrogen containing compounds provided a therapeutic effect with α methyl-D glucoside when the ratio between the α methyl-D glucoside and the nitrogen containing compound is less than 2:1. These nitrogen containing compounds include: Glycine, L-Cysteine, L-Ornthine, Cytidine, D-Asparagine, Pyrimidine, D-Alanine, D-Glucosamine HCL, DL-a-amino-n-butyric acid, Methyl(2-phenyethyl)amine Hydrochloride, and N-Acetyl-D-Glucosamine. For example, these nitrogen containing compounds provided a therapeutic effect with α methyl-D glucoside when the ratio between the α methyl-D glucoside and the nitrogen containing compound was 1:1. Not to be bound by theory, but it is believed that the higher the amount of the nitrogen containing compound in relation to the α methyl-D glucoside does not yield as positive of results because the excess nitrogen may block regulatory pathways.

Accordingly, it can be seen from the results of Table 1 that the combination of α methyl-D glucoside and certain nitrogen containing compounds, and at certain ratios between α methyl-D glucoside and the nitrogen containing compounds, provide unexpected results in achieving a soluble composition with proper pH and providing a therapeutic effect. The results are unexpected in that many of the nitrogen containing compounds did not meet such criteria at all ratios of α methyl-D glucoside to nitrogen containing compounds, and some of the nitrogen containing compounds did not provide such criteria at any ratio tested. Further, other saccharides were tested with various nitrogen sources and were unable to provide a therapeutic effect. The results of this additional testing further demonstrate the unexpected nature of the therapeutic effect that the first therapeutic agent comprising α methyl-D glucoside with a second therapeutic agent comprising certain nitrogen containing compounds provided.

It is to be noted that it is contemplated that the composition may include a first therapeutic agent including α methyl-D glucoside and a second therapeutic agent that includes one or more nitrogen containing compounds.

Accordingly, in a preferred embodiment, the urogenital composition comprises a first therapeutic agent including α methyl-D glucoside and a second therapeutic agent including a nitrogen containing compound wherein the composition synergistically effects the growth of *Lactobacillus* over *E. coli* as measured using the Therapeutic Effect Protocol described below. Preferably the composition yields a ratio of *L. crispatus* to *E. coli* greater than about 2, still more preferably greater than about 20 and still more preferably greater than 100.

The first and second therapeutic agents should be provided in an amount sufficient to provide a synergistic therapeutic effect when administered to a user. For example, where the composition comprises α methyl-D glucoside and a nitrogen containing compound as described herein present in an amount sufficient to stimulate the growth of certain healthy bacteria such as *Lactobacillus bulgaricus, Lactobacillus acidophilus, Lactobacillus gasseri, Lactobacillus crispatus, Lactobacillus casei*, and *Lactobacillus plantarum*. Generally, compositions of the present disclosure comprise less than about 10.0 wt/vol % therapeutic agents. That is to say, that the total amount of all therapeutic agents, such as the α methyl-D glucoside and the nitrogen containing compound(s), is generally less than about 10.0 wt/vol %. In particularly preferred embodiments the total amount of therapeutic agent is less than about 5.0 wt/vol % and still more preferably less than about 2.5 wt/vol %, such as from about 0.1 to about 2.0 wt/vol % percent and more preferably from about 0.2 to about 1.5 wt/vol %. For example, in one embodiment, the composition comprises from about 0.05 to about 2.0 wt/vol % α methyl-D glucoside and from about 0.05 to about 2.0 wt/vol % of a nitrogen containing compound that provides a therapeutic effect as noted above. In some embodiments, the composition comprises from about 0.1 to about 2.0 wt/vol % of α methyl-D glucoside and from about 0.1 to about 1.5 wt/vol % of the nitrogen containing compound that provides a therapeutic effect as noted above.

The compositions of the present disclosure may be formulated for administration to a user. The composition is generally applied in the form of a douche formulation, spray, moisturizer, lotion, cream, jelly, liniment, ointment, salve, oil, foam, gel, film, wash, suppository, slow-releasing polymer, coating, liquid, vaginal capsule, vaginal tablet, vaginal film, vaginal sponge, vaginal ovule, etc. The composition may also be applied to a vaginal insert, tampon, wipe or pad, and then administered to the vagina.

Formulations may comprise α methyl-D glucoside, a nitrogen containing compound, a solvent, and optionally a dermatologically acceptable carrier. As used herein, "dermatologically acceptable carrier" generally refers to a carrier that is suitable for topical application to the keratinous tissue and is compatible with a prebiotic. The dermatologically acceptable carrier may be in a wide variety of forms such as, for example, simple solutions (water-based or oil-based), solid forms (e.g. gels or sticks) and emulsions.

Solvents may be either aqueous or non-aqueous. Water is a particularly preferred aqueous solvent. Non-aqueous solvents may include, for example, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the solvent constitutes greater than about 75 wt/vol %, more preferably greater than about 85 wt/vol %, and still more preferably greater than about 90 wt/vol %.

The compositions of the present disclosure are generally acidic, i.e., have a pH less than about 7.0 and more preferably less than about 6.0, such as from about 3.0 to about 6.0 and still more preferably from about 4.0 to about 5.0. In some embodiments, a pH modifier, such as those known by ordinary skill in the art, can be added to the composition to accomplish an acidic pH. In a particularly preferred embodiment, the pH may be maintained at a mildly acidic level to correspond to normal vaginal conditions. For example, the pH may be within a range of from about 3.0 to about 6.0, in some embodiments from about 3.5 to about 5.0, and in some embodiments, from about 4.0 to about 4.5. The foregoing acidic pH may also provide other benefits. For instance, when the composition is configured to form a gel, such as described below, a low pH level may also improve the gelation rate and gel strength to reduce the likelihood of leakage just after insertion of the composition into the vagina.

In one particular preferred embodiment of the present invention, for example, the composition is configured to rapidly form a gel when applied to the vagina. A "gel" is a colloid in which a disperse phase combines with a dispersion medium to produce a jelly-like, solid or semi-solid material. The gel may form in less than about one hour, in some embodiments less than about one minute, and in some embodiments, less than about 30 seconds. Among other things, such rapid gelation reduces the likelihood of leakage during use. In addition, because the gel may form intravaginally, it is more likely to retain its structure and shape over an extended period of time. In this manner, the gel may provide the prolonged release of a therapeutic agent that inhibits and/or treats vaginal infection. For instance, the gel may remain within the vagina for about 2 to about 48 hours to provide the desired effect.

Although a variety of compounds may be employed, water is usually employed as the dispersion medium for the gel to optimize biocompatibility. Other possible dispersion mediums include non-aqueous solvents, including glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the dispersion medium (e.g., water) constitutes greater than about 75 wt/vol %, in some embodiments greater than about 90 wt/vol %, and in some embodiments, from about 95 to about 99 wt/vol % of the composition.

The disperse phase of the gel may be formed from any of a variety of different gelling agents, including temperature responsive ("thermogelling") compounds, ion responsive compounds, and so forth. Thermogelling systems, for instance, respond to a change in temperature (e.g., increase in temperature) by changing from a liquid to a gel. Generally speaking, the temperature range of interest is from about 25° C. to about 40° C., in some embodiments from about 35° C. to about 39° C., and in one particular embodiment, at the human body temperature (about 37° C.). Compositions that change state at about this temperature are useful because they will remain in a body cavity, for example, after they have been delivered. Any of a variety of thermogelling compounds that are capable of gelling when applied to the vagina may be used in the present invention. In some cases, thermogelling block copolymers, graft copolymers, and/or homopolymers may be employed. For example, polyoxyalkylene block copolymers may be used in some embodiments of the present invention to form a thermo-gelling composition. Suitable thermo-gelling compositions may include, for example, homopolymers, such as poly(N-methyl-N-n-propylacrylamide), poly(N-n-propylacrylamide), poly(N-methyl-N-isopropylacrylamide), poly(N-n-propylmethacrylamide), poly(N-isopropylacrylamide), poly(N,n-diethylacrylamide); poly(N-isopropylmethacrylamide), poly(N-cyclopropylacrylamide), poly(N-ethylmethacrylamide), poly(N-methyl-N-ethylacrylamide), poly(N-cyclopropylmethacrylamide), and poly(N-ethylacrylamide). Still other examples of suitable thermogelling polymers may include cellulose ether derivatives, such as hydroxypropyl cellulose, methyl cellulose, hydroxypropylmethyl cellulose, and ethylhydroxyethyl cellulose. Moreover thermogelling polymers may be made by preparing copolymers between (among) monomers, or by combining such homopolymers with other water-soluble polymers, such as acrylic monomers (e.g., acrylic or methacrylic acid, acrylate or methacrylate, acrylamide or methacrylamide, and derivatives thereof).

The compositions of the present invention may also include an ion responsive compound. Such compounds are generally well known in the art, and tend to form a gel in the presence of certain ions or at a certain pH. For instance, one suitable class of ion responsive compounds that may be employed in the present invention is anionic polysaccharides. Anionic polysaccharides may form a three-dimensional polymer network that functions as the disperse phase of the gel. Generally speaking, anionic polysaccharides include polysaccharides having an overall anionic charge, as well as neutral polysaccharides that contain anionic functional groups.

Any of a variety of anionic polysaccharides capable of forming a gel when contacted with vaginal mucosa may be used in the present invention. Such gel-forming anionic polysaccharides are typically stable over the normal acidic pH values found in the vagina (e.g., from about 2.5 to about 5.5). For instance, some suitable examples of gel-forming anionic polysaccharides include natural gums, such as gellan gum and alginate gums (e.g., ammonium and alkali metal of salts of alginic acid); chitosan; carboxymethylcellulose, pectins, carrageenan, xantham gum, and derivatives or salts thereof. The particular type of anionic polysaccharide selected will depend, in part, on the nature of the composition and the other components used therein. For example, carrageenan is sensitive to particular types of cations, e.g., it typically gels in the presence of potassium but not sodium. Glycuronans, likewise, typically gel in the presence of divalent cations (e.g., Ca2+), but not monovalent cations (e.g., Na+). Xanthan gum may gel in the presence of divalent cations, but only at a relatively high pH.

Although any of the above-described anionic polysaccharides may be used in the present invention, gellan gum is particularly desired for use in the present invention, either alone or in combination with other gelling agents, because it is able to form a gel in the presence of a wide variety of different cations, including both monovalent and divalent cations. Gellan gum is intended to encompass any form of gellan, including native gellan, clarified gellan, deacylated gellan, nonacylated gellan (e.g., produced from genetically engineered bacteria), clarified gellan (the polysaccharide is fully or partially removed from the bacterial debris), chemically modified gellan, etc. Various types of gellan gums and methods for forming such gums are described in U.S. Pat. Nos. 4,326,052; 4,326,053, 4,377,636; 4,385,123, and 4,563,366. Suitable gellan gums are commercially available from a variety of different sources. For example, GELRITE™ gellan gum is available from Sigma-Aldrich Chemical Co. of St. Louis, MO, and is produced from a naturally occurring polysaccharide after deacylation and clarification. Deacylated gellan is also available from CP Kelco U.S., Inc. of Chicago, IL under the name KELCO-GEL®.

Gellan gum may be either high or low acyl gellan. In the high acyl (or "native") form, two acyl substituents, acetate and glycerate, are present. Both substituents are located on the same glucose residue and, on average, there is one glycerate per repeat unit and one acetate per every two repeat units. In the low acyl form, the acyl groups may be wholly or partially removed through deacylation. The degree of deacylation of deacylated gellan gums may be at least about 20%, in some embodiments at least about 50%, and in some embodiments, at least about 75%. Alternatively, the low acyl gellan gum may simply be "nonacylated" in that it is formed without acyl groups by genetically engineered bacteria. Regardless of the manner in which they are formed, low acyl gellan gums generally have a gelation temperature within the range 30 to 50° C., which may be particularly well suited for use in the present invention so that it may gel at body temperatures of about 37° C., but remain stable at typical storage and transportation temperatures of about 25° C. In addition, low acyl gellan gums are also firm and elastic, and thus may retain their shape after delivery to the vaginal cavity.

In most embodiments the gelling agent(s) are present in an amount of from about 0.01 to about 10.0 wt/vol %, in some embodiments from about 0.05 to about 5.0 wt/vol %, and in some embodiments, from about 0.1 to about 1.0 wt/vol % of the composition.

If desired, a gelling composition may be provided in any desired form (e.g., liquid, powder, etc.). In fact, one particular benefit of the composition is that it may be administered as a liquid, which allows for the selection of a wider variety of administration techniques than would otherwise be available for a solid or semi-solid gel. One technique that may be employed includes dispensing the composition through a liquid applicator, such as a syringe or tube, into the vaginal cavity. The administered volume of the composition may constitute a single dose or two or more doses. Although not necessarily required, the composition of may also be sterilized prior to administration. Sterilization may be accomplished by any technique known in the art, such as using a gas (e.g., ethylene oxide), radiation (e.g., gamma), or heat (autoclaving). If desired, the composition may be subjected to one or more filtration steps prior to sterilization to help remove contaminants.

The urogenital compositions of the present disclosure may be applied to a suitable substrate, which in-turn may be used to apply the prebiotic composition to a user. Suitable applicators include a web, such as a wet laid tissue web or air laid web, gauze, cotton swab, transdermal patch, container or holder. Particularly preferred applicators include fibrous webs, including flushable and non-flushable cellulosic webs and nonwoven webs of synthetic fibrous material. Useful webs may be wet laid, air laid, meltblown, or spunbonded. Suitable synthetic fibrous material includes meltblown polyethylene, polypropylene, copolymers of polyethylene and polypropylene, bicomponent fibers including polyethylene or polypropylene, and the like. Useful nonwoven webs may be meltblown, coform, spunbond, airlaid, hydroentangled nonwovens, spunlace, bonded carded webs.

In certain embodiments, particularly those in which the urogenital composition is applied to a web, it may be desirable that the formulation provide certain physical attributes, such as having a smooth, lubricious, non-greasy feel; the ability to at least partially transfer from the web to the user's skin; the capability to be retained on the web at about room temperature; or the ability to be compatible with the web manufacturing process. In certain embodiments, it is preferred that at least a portion of the composition is transferred from the tissue to the user's skin in use.

The composition may be applied to a web during formation of the web or after the web has been formed and dried, often referred to as off-line or post-treatment. Suitable methods of applying the composition to a web include methods known in the art such as gravure printing, flexographic printing, spraying, WEKO™, slot die coating, or electrostatic spraying. One particularly preferred method of off-line application is rotogravure printing.

In those instances where the composition is added to the web during formation of the web and prior to drying, it may be preferred to employ an application method that incorporates the composition on the surface of the web. One method of adding the prebiotic to the web surface is by applying the composition during creping of the tissue web. Surprisingly, the composition itself may be used as a creping composition or may be combined with other well-known creping compositions to apply the composition to a tissue web without significantly degrading important web properties such as strength, stiffness or sloughing.

Fibrous webs comprising a composition made according to the present disclosure can be incorporated into multi-ply products. For instance, in one aspect, a fibrous web made according to the present disclosure can be attached to one or more other fibrous webs to form a wiping product having desired characteristics. The other webs laminated to the fibrous web of the present disclosure can be, for instance, a wet-creped web, a calendered web, an embossed web, a through-air dried web, a creped through-air dried web, an uncreped through-air dried web, an airlaid web, and the like, and may or may not comprise a prebiotic.

In other embodiments, the composition could be applied to skin to promote, maintain, or enhance the balance of a healthy microflora. Application could be as a wipe, lotion, lubricant, cream, moisturizer, patch, or other topical application methods.

In certain embodiments the composition could be ingested to promote, maintain, or enhance the balance of a healthy microflora in the gastrointestinal tract.

TEST METHODS

Therapeutic Effect Protocol

Colonies of L. crispatus and E. coli were prepared as follows. A colony of L. crispatus was transferred to 7 ml de Man, Rogosa & Sharpe (MRS) broth and incubated anaerobically (using BD GasPak EZ anaerobe container system with indicator) at 37° C. without shaking for 18-20 hours. A colony of E. coli was transferred to 5 ml Tryptic Soy Broth (TSB) and incubated aerobically (shaking at 100 rpm) at 37° C. for 18-20 hours.

Colonies were then inoculated as follows. Bacterial cultures were gently vortexed and 1 mL of each culture was transferred to a corresponding 2.0 mL micro-centrifuge tube and then centrifuged for two minutes at 14,500 rpm. The cultural supernatant was removed and the cell pellet was re-suspended in 1 mL of 0.95% (wt/vol %) saline. The re-suspended colony was then centrifuged for two minutes at 14,500 rpms and the supernatant was removed. For L. crispatus, the pellet was re-suspended in 1 mL of 0.95% saline to achieve ~$10^7$-$10^8$ cfu/mL. For E. coli, the pellet was re-suspended in 1 mL of 0.95% saline to achieve ~$10^8$-$10^9$ cfu/mL.

Media were prepared as follows.

TABLE 2

| Ingredients | g/L |
| --- | --- |
| Peptone | 15 |
| Tryptone | 10 |
| Yeast Extract | 10 |
| Tween 80 | 1 |
| α methyl-D glucoside | 1.0 |

All of the ingredients in Table 2 were combined and the pH was adjusted to 6.5. The media were then autoclaved for 20 minutes at 125° C. To evaluate the effect of various nitrogen containing therapeutic agents on the growth of bacteria, the LAPT-g media, prepared as described above, was supplemented with various nitrogen containing compound therapeutic agents to a final test concentration between 0.1 and 1.0%. As initial screening measures, solubility and initial pH of each composition were checked. If a specific composition was insoluble (as detected by visual indication of precipitates or turbidity), then no further therapeutic efficacy testing was undertaken on that composition. Additionally, if the initial pH of the composition was below 5.5 ("Low") or was above 6.5 ("High"), then no further therapeutic efficacy testing was undertaken on that composition. That is, only compositions that were soluble and had an initial pH of at or between 5.5-6.5 were used for further therapeutic efficiency testing as follows.

Five milliliters (5 mL) of each medium was transferred to a test tube in duplicates for subsequent inoculation. A master mixture of L. crispatus and E. coli, prepared as described above, was prepared in 1,000:1 ratio. Each (5 ml) test tube was inoculated with the master mixture to give $10^5$-$10^6$ total CFU L. crispatus and 100-1,000 total CFU E. coli per tube.

To establish a negative control, one tube was vortexed and 100 μL was removed to determine the initial cell concentrations by serial dilutions and plating (2 plates per dilution). L. crispatus is selected on MRS agar plates incubated anaerobically at 37° C. for two days. E. coli is selected on TSA plates incubated aerobically at 37° C. for one day. The co-cultures were incubated in an anaerobic container with BD GasPaks at 37° C. for 36 hours.

The effect of the α methyl-D glucoside and the nitrogen containing compound therapeutic agents on the ratio of L. crispatus to E. coli was measured 36 hours after inoculation and a final pH of the test solutions was recorded. The co-culture tube was vortexed and 100 μL was removed to determine the final cell concentrations by serial dilutions and plating (2 plates per dilution). L. crispatus is selected on MRS agar plates incubated anaerobically at 37° C. for two days. *E. coli* is selected on TSA plates incubated aerobically at 37° C. for one day.

EMBODIMENTS

In view of the foregoing description and examples, the present disclosure provides the following embodiments.

Embodiment 1: A composition comprising: a first therapeutic agent comprising α methyl-D glucoside; and a second therapeutic agent comprising a nitrogen containing compound, the nitrogen containing compound selected from the group consisting of L-Cysteine, Cytidine, D-Asparagine, Pyrimidine, D-Alanine, D-glucosamine HCL, and N-Acetyl-D-Glucosamine.

Embodiment 2: The composition of embodiment 1, wherein a weight ratio between the first therapeutic agent and the second therapeutic agent is from about 0.5:1 to about 20:1.

Embodiment 3: The composition of embodiment 2, wherein the weight ratio is about 1:1 to about 10:1.

Embodiment 4: The composition of any of the preceding embodiments, wherein the first therapeutic agent comprises from about 0.1 wt/vol % to about 2.0 wt/vol % of the composition and the second therapeutic agent comprises from about 0.1 wt/vol % to about 2.0 wt/vol %.

Embodiment 5: The composition of any of the preceding embodiments, wherein the composition synergistically promotes the growth of *Lactobacilli* relative to *E. coli* such that the therapeutic effect is greater than about 2.

Embodiment 6: The composition of any of the preceding embodiments, further comprising a dispersion medium and a gelling agent.

Embodiment 7: A composition comprising: a first therapeutic agent comprising α methyl-D glucoside; and a second therapeutic agent comprising a nitrogen containing compound, the nitrogen containing compound selected from the group consisting of: Alloxan, Ammonium Citrate, Glycine, L-Cysteine, L-Glutamic Acid, L-Glutamine, L-Homoserine, L-Leucine, L-Lysine, L-Methionine, L-Tyrosine, Cytidine, D-Asparagine, Adenosine, H-Ala Thr-OH, D-glucoronamide, Ala-asp, Ala-His, Gly-Met, N-Acetyl-D-Galactosamine, Pyrimidine, L-Serine, Inosine, D-Alanine, N-Acetyl-D-Mannosamine, Gly-Asn, Ala-Glu, D-Galactosamine HCL, D-Glucosamine HCL, DL-a-amino-n-butyric acid, D-mannosamine HCl, Gly-Gln, Gly-Glu, DL Lactamide, Met-Ala, Methyl(2-phenylethyl)amine Hydrochloride, Glycyl-Alanine, DL-gamma-amino-n-butyric acid, and N-Acetyl-D-Glucosamine; wherein a weight ratio between the first therapeutic agent and the second therapeutic agent is at least about 2:1.

Embodiment 8: The composition of embodiment 7, wherein the weight ratio between the first therapeutic agent and the second therapeutic agent is less than about 20:1.

Embodiment 9: The composition of embodiment 7 or 8, wherein the composition synergistically promotes the growth of *Lactobacilli* relative to *E. coli* such that the therapeutic effect is greater than about 2.

Embodiment 10: The composition of any one of embodiments 7-9, wherein the first therapeutic agent comprises from about 0.1 wt/vol % to about 2.0 wt/vol % of the composition and the second therapeutic agent comprises from about 0.1 wt/vol % to about 1.0 wt/vol %.

Embodiment 11: The composition of any one of embodiments 7-10, wherein the nitrogen containing compound is selected from the group consisting of Alloxan, L-Cysteine, Cytidine, D-Asparagine, H-Ala Thr-OH, D-glucoronamide, Ala-His, Gly-Met, N-Acetyl-D-Galactosamine, Pyrimidine, L-Serine, Inosine, D-Alanine, Gly-Asn, D-Galactosamine HCL, D-Glucosamine HCL, Gly-Gln, DL Lactamide, and N-Acetyl-D-Glucosamine, and wherein the weight ratio between the first therapeutic agent and the second therapeutic agent is less than about 20:1.

Embodiment 12: The composition of any one of embodiments 7-10, wherein the nitrogen containing compound is selected from the group consisting of Alloxan, Glycine, L-Cysteine, Cytidine, D-Asparagine, H-Ala Thr-OH, D-glucoronamide, Ala-His, Gly-Met, N-Acetyl-D-Galactosamine, Pyrimidine, L-Serine, Inosine, D-Alanine, N-Acetyl-D-Mannosamine, Gly-Asn, D-Galactosamine HCL, D-Glucosamine HCL, DL-a-amino-n-butyric acid, D-mannosamine HCl, Gly-Gln, DL Lactamide, Glycyl-Alanine, DL-gamma-amino-n-butyric acid, and N-Acetyl-D-Glucosamine; and wherein the weight ratio between the first therapeutic agent and the second therapeutic agent is from about 2:1 to about 5:1.

Embodiment 13: The composition of any one of embodiments 7-10, wherein the nitrogen containing compound is selected from the group consisting of Alloxan, Ammonium Citrate, L-Cysteine, L-Glutamic Acid, L-Glutamine, L-Homoserine, L-Leucine, L-Lysine, L-Methionine, L-Tyrosine, Cytidine, D-Asparagine, Adenosine, H-Ala Thr-OH, D-glucoronamide, Ala-asp, Ala-His, Gly-Met, N-Acetyl-D-Galactosamine, Pyrimidine, L-Serine, Inosine, D-Alanine, Gly-Asn, Ala-Glu, D-Galactosamine HCL, D-Glucosamine HCL, Gly-Gln, Gly-Glu, DL Lactamide, Met-Ala, Methyl (2-phenylethyl)amine Hydrochloride, and N-Acetyl-D-Glucosamine; and wherein the weight ratio between the first therapeutic agent and the second therapeutic agent is from about 10:1 to about 20:1.

Embodiment 14: The composition of embodiment 13, wherein the weight ratio between the first therapeutic agent and the second therapeutic agent is about 10:1.

Embodiment 15: The composition of any one of embodiments 7-14, further comprising a dispersion medium and a gelling agent.

Embodiment 16: A composition comprising: a first therapeutic agent comprising α methyl-D glucoside; and a second therapeutic agent comprising a nitrogen containing compound, the nitrogen containing compound selected from the group consisting of Glycine, L-Cysteine, L-Ornthine, Cytidine, D-Asparagine, Pyrimidine, D-Alanine, D-Glucosamine HCL, DL-a-amino-n-butyric acid, Methyl(2-phenyethyl)amine Hydrochloride, and N-Acetyl-D-Glucosamine; wherein a weight ratio between the first therapeutic agent and the second therapeutic agent is less than about 2:1.

Embodiment 17: The composition of embodiment 16, wherein the weight ratio between the first therapeutic agent and the second therapeutic agent is about 1:1.

Embodiment 18: The composition of embodiment 16 or 17, wherein the first therapeutic agent comprises from about 0.1 wt/vol % to about 2.0 wt/vol % of the composition and the second therapeutic agent comprises from about 0.1 wt/vol % to about 2.0 wt/vol %.

Embodiment 19: The composition of any one of embodiments 16-18, wherein the composition synergistically promotes the growth of *Lactobacilli* relative to *E. coli* such that the therapeutic effect is greater than about 2.

Embodiment 20: A method for maintaining a healthy microflora balance in the urogenital area of a patient in need thereof, the method comprising topically administering to the urogenital area of the patient a composition comprising a first therapeutic agent comprising α methyl-D glucoside and a second therapeutic agent, the second therapeutic agent comprising a nitrogen containing compound, the nitrogen containing compound selected from the group consisting of Alloxan, Ammonium Citrate, Glycine, L-Cysteine, L-Glutamic Acid, L-Glutamine, L-Homoserine, L-Leucine, L-Lysine, L-Methionine, L-Ornthine, L-Tyrosine, Cytidine, D-Asparagine, Adenosine, H-Ala-Thr-OH, D-glucoronamide, Ala-Asp, Ala-His, Gly-Met, N-Acetyl-D-Galactosamine, Pyrimidine, L-Serine, Inosine, D-Alanine, N-Acetyl-D-Mannosamine, Gly-Asn, Ala-Glu, D-Galactosamine HCL, D-glucosamine HCL, DL-a-amino-n-butyric acid, D-mannosamine HCL, Gly-Gln, Gly-Glu, DL Lactamide, Met-Ala, Methyl(2-phenylehtyl)amine Hydrochloride, Glycyl-Alanine, DL-gamma-amino-n-butyric acid, and N-Acetyl-D-Glucosamine; wherein the administration of the composition increases lactobacillus growth or activity in vivo relative to *E. coli.*

Embodiment 21: The method of embodiment 20, wherein the nitrogen containing compound is selected from the group consisting of: the nitrogen containing compound selected from the group consisting of L-Cysteine, Cytidine, D-Asparagine, Pyrimidine, D-Alanine, D-glucosamine HCL, and N-Acetyl-D-Glucosamine, and wherein a weight ratio between the first therapeutic agent and the second therapeutic agent is from about 0.5:1 to about 20:1.

Embodiment 22: The method of embodiment 20 or 21, wherein the nitrogen containing compound is selected from the group consisting of: Alloxan, Ammonium Citrate, Glycine, L-Cysteine, L-Glutamic Acid, L-Glutamine, L-Homoserine, L-Leucine, L-Lysine, L-Methionine, L-Tyrosine, Cytidine, D-Asparagine, Adenosine, H-Ala Thr-OH, D-glucoronamide, Ala-asp, Ala-His, Gly-Met, N-Acetyl-D-Galactosamine, Pyrimidine, L-Serine, Inosine, D-Alanine, N-Acetyl-D-Mannosamine, Gly-Asn, Ala-Glu, D-Galactosamine HCL, D-Glucosamine HCL, DL-a-amino-n-butyric acid, D-mannosamine HCl, Gly-Gln, Gly-Glu, DL Lactamide, Met-Ala, Methyl(2-phenylethyl)amine Hydrochloride, Glycyl-Alanine, DL-gamma-amino-n-butyric acid, and N-Acetyl-D-Glucosamine; and wherein a weight ratio between the first therapeutic agent and the second therapeutic agent is at least about 2:1.

Embodiment 23: The method of embodiment 20, wherein the nitrogen containing compound is selected from the group consisting of Alloxan, L-Cysteine, Cytidine, D-Asparagine, H-Ala Thr-OH, D-glucoronamide, Ala-His, Gly-Met, N-Acetyl-D-Galactosamine, Pyrimidine, L-Serine, Inosine, D-Alanine, Gly-Asn, D-Galactosamine HCL, D-Glucosamine HCL, Gly-Gln, DL Lactamide, and N-Acetyl-D-Glucosamine; and wherein a weight ratio between the first therapeutic agent and the second therapeutic agent from about 2:1 to about 20:1.

Embodiment 24: The method of embodiment 20, wherein the nitrogen containing compound is selected from the group consisting of Alloxan, Glycine, L-Cysteine, Cytidine, D-Asparagine, H-Ala Thr-OH, D-glucoronamide, Ala-His, Gly-Met, N-Acetyl-D-Galactosamine, Pyrimidine, L-Serine, Inosine, D-Alanine, N-Acetyl-D-Mannosamine, Gly-Asn, D-Galactosamine HCL, D-Glucosamine HCL, DL-a-amino-n-butyric acid, D-mannosamine HCl, Gly-Gln, DL Lactamide, Glycyl-Alanine, DL-gamma-amino-n-butyric acid, and N-Acetyl-D-Glucosamine; and wherein a weight ratio between the first therapeutic agent and the second therapeutic agent is from about 2:1 to about 5:1.

Embodiment 25: The method of embodiment 20, wherein the nitrogen containing compound is selected from the group consisting of Alloxan, Ammonium Citrate, L-Cysteine, L-Glutamic Acid, L-Glutamine, L-Homoserine, L-Leucine, L-Lysine, L-Methionine, L-Tyrosine, Cytidine, D-Asparagine, Adenosine, H-Ala Thr-OH, D-glucoronamide, Ala-asp, Ala-His, Gly-Met, N-Acetyl-D-Galactosamine, Pyrimidine, L-Serine, Inosine, D-Alanine, Gly-Asn, Ala-Glu, D-Galactosamine HCL, D-Glucosamine HCL, Gly-Gln, Gly-Glu, DL Lactamide, Met-Ala, Methyl(2-phenylethyl)amine Hydrochloride, and N-Acetyl-D-Glucosamine; and wherein a weight ratio between the first therapeutic agent and the second therapeutic agent is from about 10:1 to about 20:1.

Embodiment 26: The method of embodiment 20, wherein the nitrogen containing compound is selected from the group consisting of Glycine, L-Cysteine, L-Ornthine, Cytidine, D-Asparagine, Pyrimidine, D-Alanine, D-Glucosamine HCL, DL-a-amino-n-butyric acid, Methyl(2-phenyethyl)amine Hydrochloride, and N-Acetyl-D-Glucosamine; and wherein a weight ratio between the first therapeutic agent and the second therapeutic agent is less than about 2:1.

Embodiment 27: The method of any one of embodiments 20-26, wherein the first therapeutic agent comprises from about 0.1 wt/vol % to about 2.0 wt/vol % of the composition and the second therapeutic agent comprises from about 0.1 wt/vol % to about 2.0 wt/vol %.

What is claimed is:

1. A method for maintaining a healthy microflora balance in the urogenital area of a patient, the method comprising topically administering to the urogenital area of the patient a composition comprising a first therapeutic agent comprising α methyl-D glucoside and a second therapeutic agent, the second therapeutic agent comprising a nitrogen containing compound, the nitrogen containing compound selected from the group consisting of Pyrimidine, D-glucosamine HCL, and N-Acetyl-D-Glucosamine;
    wherein a weight ratio between the first therapeutic agent and the second therapeutic agent is from about 0.5:1 to about 20:1, and wherein the administration of the composition increases *lactobacillus* growth or activity in vivo relative to *E. coli.*

2. A method for maintaining a healthy microflora balance in the urogenital area of a patient, the method comprising topically administering to the urogenital area of the patient a composition comprising a first therapeutic agent comprising α methyl-D glucoside and a second therapeutic agent, the second therapeutic agent comprising a nitrogen containing compound, wherein the nitrogen containing compound is selected from the group consisting of: Alloxan, Ammonium Citrate, Glycine, L-Glutamic Acid, L-Glutamine, L-Homoserine, L-Leucine, L-Lysine, L-Methionine, L-Tyrosine, Adenosine, H-Ala Thr-OH, D-glucoronamide, Ala-asp, Ala-His, Gly-Met, N-Acetyl-D-Galactosamine, L-Serine, Inosine, N-Acetyl-D-Mannosamine, Gly-Asn, Ala-Glu, D-Galactosamine HCL, DL-a-amino-n-butyric acid, D-mannosamine HCl, Gly-Gln, Gly-Glu, DL Lactamide, Met-Ala, Methyl(2-phenylethyl)amine Hydrochloride, Glycyl-Alanine, and DL-gamma-amino-n-butyric acid;
    and wherein a weight ratio between the first therapeutic agent and the second therapeutic agent is from about 2:1 to about 20:1, and wherein the administration of the composition increases *lactobacillus* growth or activity in vivo relative to *E. coli.*

3. The method of claim 2, wherein the nitrogen containing compound is selected from the group consisting of Alloxan, H-Ala Thr-OH, D-glucoronamide, Ala-His, Gly-Met, N-Acetyl-D-Galactosamine, L-Serine, Inosine, Gly-Asn, D-Galactosamine HCL, and Gly-Gln, DL Lactamide.

4. The method of claim 2, wherein the nitrogen containing compound is selected from the group consisting of Alloxan, Glycine, H-Ala Thr-OH, D-glucoronamide, Ala-His, Gly- Met, N-Acetyl-D-Galactosamine, L-Serine, Inosine, N-Acetyl-D-Mannosamine, Gly-Asn, D-Galactosamine HCL, DL-a-amino-n-butyric acid, D-mannosamine HCl, Gly-Gln, DL Lactamide, Glycyl-Alanine, and DL-gamma-amino-n-butyric acid;

and wherein the weight ratio between the first therapeutic agent and the second therapeutic agent is from about 2:1 to about 5:1.

5. The method of claim 2, wherein the nitrogen containing compound is selected from the group consisting of Alloxan, Ammonium Citrate, L-Glutamic Acid, L-Glutamine, L-Homoserine, L-Leucine, L-Lysine, L-Methionine, L-Tyrosine, Adenosine, H-Ala Thr-OH, D-glucoronamide, Ala-asp, Ala-His, Gly-Met, N-Acetyl-D-Galactosamine, L-Serine, Inosine, Gly-Asn, Ala-Glu, D-Galactosamine HCL, Gly-Gln, Gly-Glu, DL Lactamide, Met-Ala, and Methyl(2-phenyl-ethyl)amine Hydrochloride; and wherein the weight ratio between the first therapeutic agent and the second therapeutic agent is from about 10:1 to about 20:1.

6. A method for maintaining a healthy microflora balance in the urogenital area of a patient, the method comprising topically administering to the urogenital area of the patient a composition comprising a first therapeutic agent comprising α methyl-D glucoside and a second therapeutic agent, the second therapeutic agent comprising a nitrogen containing compound, wherein the nitrogen containing compound is selected from the group consisting of Glycine, L-Ornthine, DL-a-amino-n-butyric acid, and Methyl(2-phenyethyl)amine Hydrochloride;

and wherein a weight ratio between the first therapeutic agent and the second therapeutic agent is less than about 2:1, and wherein the administration of the composition increases *lactobacillus* growth or activity in vivo relative to *E. coli*.

7. The method of claim 1, wherein the first therapeutic agent comprises from about 0.1 wt/vol % to about 2.0 wt/vol % of the composition and the second therapeutic agent comprises from about 0.1 wt/vol % to about 2.0 wt/vol %.

8. The method of claim 2, wherein the first therapeutic agent comprises from about 0.1 wt/vol % to about 2.0 wt/vol % of the composition and the second therapeutic agent comprises from about 0.1 wt/vol % to about 2.0 wt/vol %.

9. The method of claim 6, wherein the first therapeutic agent comprises from about 0.1 wt/vol % to about 2.0 wt/vol % of the composition and the second therapeutic agent comprises from about 0.1 wt/vol % to about 2.0 wt/vol %.

10. The method of claim 1, wherein a total amount of the α methyl-D glucoside and the nitrogen containing compound is from 0.1 to 10.0 wt/vol %.

11. The method of claim 2, wherein a total amount of the α methyl-D glucoside and the nitrogen containing compound is from 0.1 to 10.0 wt/vol %.

12. The method of claim 6, wherein a total amount of the α methyl-D glucoside and the nitrogen containing compound is from 0.1 to 10.0 wt/vol %.

13. The method of claim 6, wherein the weight ratio between the first therapeutic agent and the second therapeutic agent is greater than about 0.5:1.

* * * * *